(12) United States Patent
Little, III

(10) Patent No.: US 9,057,718 B2
(45) Date of Patent: Jun. 16, 2015

(54) OPTICAL DETERMINATION AND REPORTING OF HYDROCARBON PROPERTIES

(75) Inventor: Joseph Paul Little, III, Austin, TX (US)

(73) Assignee: JP3 Measurement, LLC, Austin, TX (US)

(*) Notice: Subject to any disclaimer, the term of this patent is extended or adjusted under 35 U.S.C. 154(b) by 1941 days.

(21) Appl. No.: 11/419,241

(22) Filed: May 19, 2006

(65) Prior Publication Data

US 2007/0082407 A1    Apr. 12, 2007

Related U.S. Application Data

(60) Provisional application No. 60/761,981, filed on Jan. 25, 2006, provisional application No. 60/724,025, filed on Oct. 6, 2005.

(51) Int. Cl.

| | | |
|---|---|---|
| *G01N 33/00* | (2006.01) | |
| *G01N 33/24* | (2006.01) | |
| G01N 21/3504 | (2014.01) | |
| G01N 21/359 | (2014.01) | |
| G06F 17/00 | (2006.01) | |
| G01N 21/00 | (2006.01) | |

(52) U.S. Cl.
CPC .............. *G01N 33/241* (2013.01); *Y10T 436/21* (2015.01); *G01N 21/359* (2013.01); *G01N 21/3504* (2013.01)

(58) Field of Classification Search
CPC . G06Q 50/06; G01N 21/3504; G01N 21/359; G01N 33/241
USPC .................... 705/400; 436/164, 139
See application file for complete search history.

(56) References Cited

U.S. PATENT DOCUMENTS

| | | | | |
|---|---|---|---|---|
| 6,157,455 A | * | 12/2000 | Pinvidic et al. ............... | 356/437 |
| 2004/0204775 A1 | * | 10/2004 | Keyes et al. .................... | 700/29 |

OTHER PUBLICATIONS

Workman, Jerrome (Jerry), "An Introduction to Near infrared spectroscopy" online article, Sep. 12, 2005, p. 1-6, <www.spectroscopynow.com>.*

* cited by examiner

*Primary Examiner* — Dennis M White
*Assistant Examiner* — Bryan Kilpatrick
(74) *Attorney, Agent, or Firm* — DuBois, Bryant & Campbell LLP; William D. Wiese

(57) ABSTRACT

A chemical composition analyzer may be used to optically determine and report chemical compositions associated with natural gases within a gas collection and transmission infrastructure. This analyzer includes a number of optical sensors which may be used to perform spectroscopic spectrographic analysis in order to determine the chemical composition of the natural gas. Additionally other sensors may be used to measure other physical properties associated with the natural gas. These sensors are tied to a data collection system wherein the output of the optical sensors and sensors used to measure the physical properties of the natural gas may be combined and processed in order to determine in a nearly continuous fashion the chemical composition associated with the natural gas at various locations within the gas collection and transmission infrastructure. This real time compositional analysis may be used to determine valuations of the gas or to optimize other processes or equipment configurations.

27 Claims, 6 Drawing Sheets

OPTICAL DETERMINATION AND REPORTING OF HYDROCARBON PROPERTIES

RELATED APPLICATIONS

This application claims priority under 35 USC §119 (e) to and incorporates by reference for all purposes the provisionally filed patent application entitled "Spectrographic Analysis of Hydrocarbons," Ser. No. 60/724,025 filed on Oct. 6, 2005 to inventor Paul Little and provisionally filed patent application entitled "Communication and Reporting of Optically Measured Properties of Hydrocarbons," Ser. No. 60/761,981 filed on Jan. 25, 2006 to inventor Paul Little.

TECHNICAL FIELD OF THE INVENTION

The present invention relates generally to chemical analysis systems and methods, and more particularly, a system and method to optically determine chemical properties of a gas.

BACKGROUND OF THE INVENTION

Current practices use gas chromatography (GC) to periodically sample natural gas to determine the chemical composition within a gas collection and transmission facility. For example, gas chromatography is often performed on a monthly or quarterly basis to determine the health of an individual well or field. These samples are then used to determine the quality, energy content, or pricing associated with the gas delivered from that well or field. However, changes in the gas content, for the better or worse, may result in unrealized profits from a well or field. In the case of declining quality, penalties may be imposed on the supplier by delivering product from a field that does not meet the previously stated product requirements. Thus, using only one sample to describe the quality of the gas for an entire quarter is unrealistic.

In another instance, these samples may be taken at a single gathering location which pools gases supplied from a number of wells or fields. As not all the wells may be on service at the time of the sample, the removal from service of a high energy well may adversely impact the measured quality. When the high energy well is returned to serve, the output from the gathering location may then be undervalued because for an entire quarter or until the next periodic sample. This is because the high energy content is not considered.

Additionally, the potentially large latency between samples may result in undetected rising levels of contaminants such as hydrogen sulfide, carbon dioxide, water, nitrogen, and other like contaminates that do not contribute to the energy content of the gas. This may result in the gases exceeding the specified levels during the periodicity between samples. This in turn may result in damage to processing or manufacturing equipment and fines for the supplier.

SUMMARY OF THE INVENTION

The present invention provides a system and method that substantially eliminates or reduces disadvantages and problems associated with previously developed chemical analysis systems and methods used to determine the content of natural gas.

The chemical composition of the natural gas within a gas collection and transmission infrastructure may be measured using optical sensors that perform spectrographic analysis. These sensors may be placed at various locations within the gas collection and transmission infrastructure and may be monitored locally or remotely. Additionally other sensors may be used to measure physical properties associated with the natural gas. The remote optical sensors and other sensors may be communicatively coupled to a data gathering location. This allows the sensors to report the chemical composition end physical properties associated with the natural gas. Processing modules within the data gathering location or having access to the data gathering location then may determine the chemical composition associated with the natural gas. In one embodiment, the present invention determines the energy content, specific gravity, compressibility, hydrogen dew point, moisture content, and Wobbe index of the natural gas which may then be used to determine the pricing structures or equipment configurations necessary to properly and efficiently process the natural gas.

A second embodiment, as alluded to previously, may be used to specifically determine the configuration of a natural gas processor module or other equipment associated with a natural gas collection, transmission and/or processing infrastructure. (i.e. The required scrubbing equipment may be identified based on the chemical composition of the natural gas.) As before the chemical composition of the natural gas may be measured using remote optical sensors that perform spectrographic analysis. Other properties (such as but not limited to pressure and temperature) associated with the natural gas may be determined as well. These remote sensors may be communicatively coupled to a data gathering location in order to report the chemical composition and physical properties associated with the natural gas. Having this information allows downstream processing and manufacturing equipment to be more efficiently or optimally configured in order to properly process the natural gas based on current market conditions, the end users needs, specifications, energy contents contaminants, or other qualities found in the chemical composition.

Another embodiment provides a chemical composition analyzer that may be used to optically determine and report the chemical composition of the natural gas within a gas collection and transmission infrastructure. This analyzer has a number of remote optical sensors that perform spectrographic analysis to measure or determine the chemical composition of the natural gas. Additionally other sensors may be used to measure the physical properties associated with the natural gas. Data collection and processing systems will couple to the sensors. This allows the output of the sensors to be processed using the data collection and processing system in order to determine in a real or quasi real time the chemical composition associated with the quantities of natural gas currently present within the gas collection and transmission infrastructure.

The information associated with determining the chemical composition of the natural gas may be used to schedule or identify the need for maintenance within the gas collection infrastructure. In one example this may be the need to further perforate a well. This may involve maintenance to the wells, handling equipment, or other maintenance or repair activities associated with the gas collection and processing infrastructure. Similarly this knowledge of the chemical composition and other properties associated with the natural gas on a more frequent or continuous basis than was previously available allows one to properly and more accurately determine the energy content of the natural gas as it varies over time. This allows a more accurate pricing structure to be determined and implemented. Embodiments of the present invention also enable companies to characterize their reserves as the gas changes over time in order to derive a fair net present value and plan production.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGUREs, like numerals being used to refer to like and corresponding parts of the various drawings.

Embodiments of the present invention provide a way of optically determining the chemical composition of natural gas to derive the energy content (expressed in British Thermal Units (BTU)), hydrocarbon dew point, compressibility, specific gravity, moisture content, impurities, Wobbe index and other like properties associated with hydrocarbons such as but not limited to natural gas. Embodiments may employ the Near Infrared band of the electromagnetic spectrum, specifically between the 1300 nm to 2500 nm range. We will be focusing on the 1550 nm to 1800 nm range to resolve the chemicals that contribute energy content to natural gas. This is a C—H overtone region of the spectrum.

Another embodiment of the present invention provides a way of electronically gathering and reporting optically determined chemical compositions of natural gas. The invention describes an on-line process of gathering, transmitting, and storing data obtained using the NIR band of the electromagnetic spectrum, specifically between the 1300 nm to 2500 nm range. The information may be used to make various business, maintenance, and processing decisions based on the real-time feed or historically trended data from the instruments.

Micro-electromechanical machining processes have produced compact, reliable equipment capable of high resolution spectrographic analysis with very low power consumption. The low power consumption, small size, and readily available powerful micro-computing components enable these components to be remotely installed throughout a natural gas collection and transmission infrastructure. Gases, such as but not limited to natural gas are bought and sold based on volume and energy content. Significant interest, especially at custody transfer points, exists in the ability to have a quick and accurate measurement of energy content, hydrocarbon dew point, compressibility, specific gravity, moisture content, and Wobbe index values. These installations will lead to a much more efficient and accurate market place.

NIR spectrographic analysis provides a non-invasive optical measurement that has no emissions. Further, there is no need for calibration gases or carrier gases to perform measurements as with traditional gas chromatography. Traditional remote site chromatographs need a calibration gas bottle and a carrier gas bottle approximately every 6 months. In addition to the consumable costs, the separation columns in the in the gas chromatographs (GCs) have a tendency to get clogged and need replacement. Unlike GCs, occasional liquid condensate introduction will not destroy expensive components in an NIR spectrometer. Therefore, NIR spectrographic analysis allows a more environmentally friendly, and significantly cheaper cost of ownership than conventional chromatography.

Figure 1:
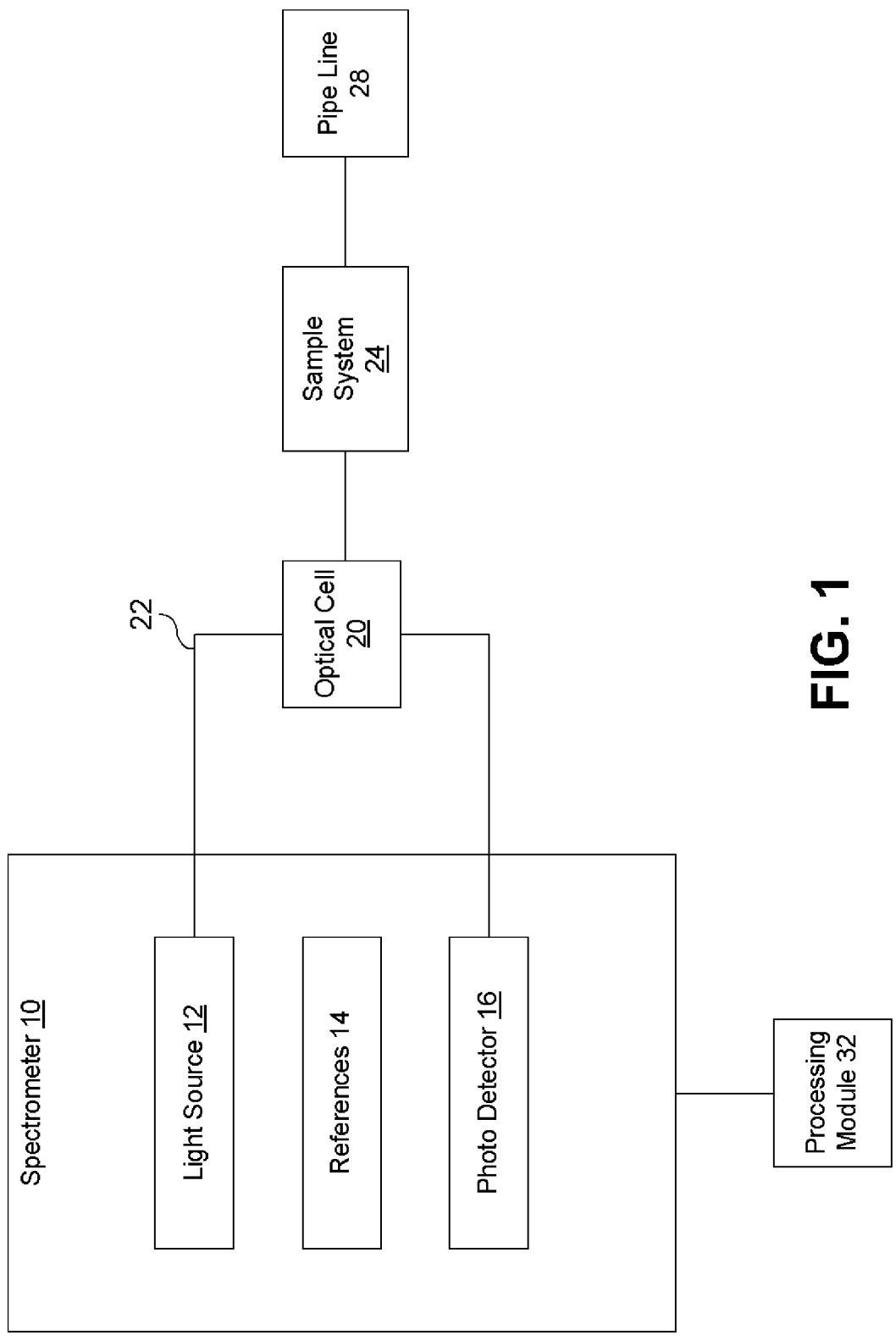
FIG. 1 provides a block diagram of a spectrograph operable to perform spectrographic analysis of gases in the field in accordance with an embodiment that may be used in accordance with an embodiment of the present invention.

An exemplary spectrograph 10 shown in FIG. 1 may be used by embodiments of the present invention includes a light source 12, integrated wavelength and amplitude references 14, and a photo detector 16. The light source 12 will preferably be a tunable diode laser. Spectrograph 10 will be coupled to an optical gas cell 20 via fiber optic cables 22. A sample system 24 will extract gas 26 from the pipe line 28, measure the pressure and temperature of the gas, direct the gas through optical cell 20 where it will be exposed to light from the light source 12, and reintroduce the sample in the transmission line 28 or exhaust it. The sample system may need to be heated in certain installations in order to keep the gas above the dew point temperature. The spectral data will be transmitted back to the photo detector 16 via the fiber optic cables 22. The detector array will preferably be an Indium Gallium Arsenide (InGaAs) photo detector. Electronics (processing module 32) will process the spectrographic image to determine the image's energy content and chemical composition. Other properties of the gas such as hydrocarbon dew point, specific gravity, compressibility, and Wobbe index can also be computed from the compositional information. The results will then be stored for a later transmission and analysis or sent directly to a data gathering location.

The processing module 32 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processing module 32 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The processing module 32 executes, operational instructions corresponding to at least some of the steps and/or functions illustrated in FIG. 6.

Embodiments of the present invention may employ chemometeric models and other analytical techniques to determine the composition of the gas 26. The data models are used to compare the spectrums being gathered by spectrograph 10 from the gas 26 flowing through the sample cell 20 with known results. The models will be built from a variety of different sources. Parts of the models are created by correlating output values from a GC with the spectrum of the same gas. In addition to the GC correlation, one may mix gasses of known composition and record their respective spectrums using the spectrograph. Pressure and temperature will be recorded to account for their effects. Any offsets or adjustments required will be included in the calibration models. All of this information is compiled and used as a reference to compare the information coming from the on-line monitor. The calibration set will allow one to derive the sample's energy content in both dry and saturated states, compressibility, hydrocarbon dew point, moisture content, specific gravity, Wobbe index and other like information.

Embodiments of the present invention have the ability to transmit the data back to a gathering location to keep a recorded history of values. The transmission can be wireless or via hard wire. Some configurations may perform data processing on-board while others will send raw data that will be processed by another computer that has the chemometric models and analytical software.

Power may be provided by a rechargeable battery source that can be replenished by solar power, generator, or hard line electricity. The direct current of the battery source runs through an inverter to achieve alternating current of a 120 or 240 volts @ 60 hertz. This may be used to power the spectrometer, light source 12, the on-board computing module, pressure transducers, temperature sensing modules, any heating elements, data transmitting equipment, and the valve control manifold for the sampling system. This reduces the required infrastructure needed to support the sensors in the field.

Figure 2:
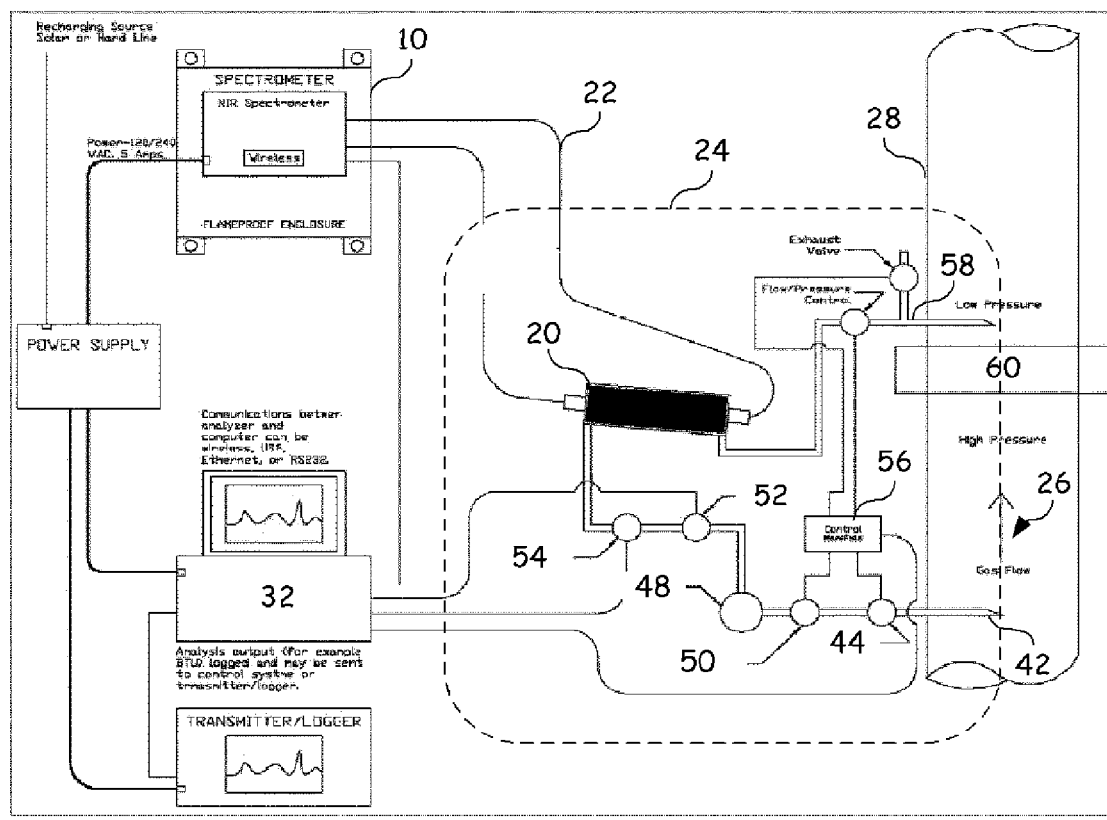
FIG. 2 provides a sample system used in combination with the spectrograph of FIG. 1 in accordance with an embodiment of the present invention.

Sampling system 24 as shown in FIG. 2 will include sample probe 42 to extract gas 26 from the transmission line 28, a shut off valve 44, a switching valve, a filter 48, a flow controller or regulator 50, a pressure transducer 52, a temperature probe 54, an optical cell 20 coupled with fiber optic cables 22, a beater operable to heat the sampled gas, another flow controller or regulator 56, and a connection 58 to reintroduce the sample gas or exhaust the sampled gas. The sample system will preferably operate across a constriction point 60 in transmission line 28 in order to create a pressure differential to flow gas though the sample loop. Due to the fact that optical measurement is non-invasive, the sample may be reintroduced into the gas transmission line 28 but may be exhausted if the site set-up is not conducive to reintroduction. A small pump may be used for reintroduction if no pressure delta can readily be established. Sample loop valves may be actuated by a switching manifold controlled by the on-board electronics. The pressure and temperature sensors provide data signals to the on-board electronics to be included in the data log for each respective spectral recording. The signals will probably be 4-20 ma analog signals. Pressure through the sampling system will probably be around 100 psi, although other pressures both higher and lower are contemplated. The gas cell will be at an angle such that any liquids that may condense can flow out and not build up in the cell. These spectrographs may be repeated on the order of every 20 milliseconds or as specified by data management requirements. In some embodiments but not all, the spectrograph and electronics may be housed in an enclosure that is explosion proof and rated for Div. 1 Class 1 environments.

Figure 3:
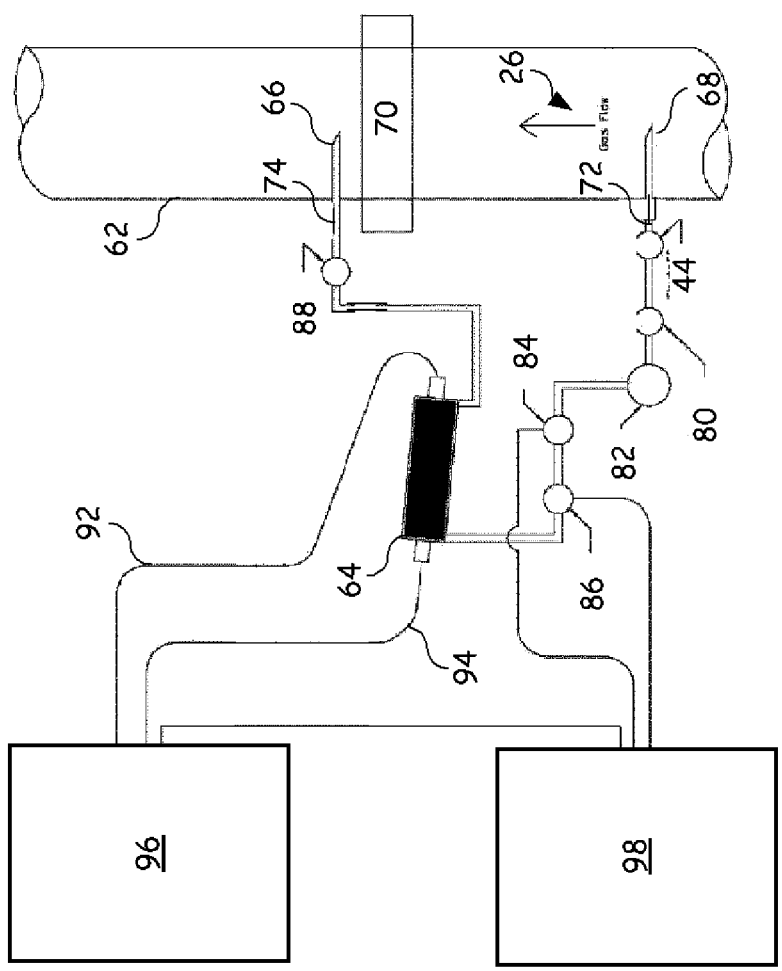
FIG. 3 depicts a another embodiment in accordance with the present invention wherein a remote optical sensor is used coupled to a gas collection or transmission system in accordance with an embodiment of the present invention.

FIG. 3 shows another embodiment of the present invention wherein a remote optical sensor is used to couple to a gas collection and/or transmission system. Here gas flow 26 within a piping infrastructure 62 has a series of physical and chemical properties associated with the gas. As shown here optical cell 64 is placed between a low pressure tap 66 and high pressure tap 68 through which sample gas flows. Differential pressure drives flow through optical cell 64 is provided by a restrictor or volume metering device 70. This embodiment and that as shown in FIG. 2, show how optical cell 64 may be placed in sample lines which may have been previously used to take gas samples which would have been processed using gas chromatography. High pressure sample line 72 and low pressure sample line 74 may be isolated from the gas flow 26 using shutoff valves. A flow pressure controller 80 is used to control the amount of flow to optical cell 64. Additionally gas flow may be filtered using a gas filter 82. Physical parameters associated with the gas such as but not limited to pressure and temperature may be measured using pressure sensor 84 and temperature sensor 86 respectively. Gas flow through optical cell 64 is returned through the low pressure line 66 which may further include a low pressure controller 88 wherein flow pressure controller 80 and 88 may be controlled using a control manifold.

Fiber optic cables 92 and 94 may be used to couple optical cell 64 to spectrometer 96. As described previously this spectrometer may be a NIR spectrometer in order to more efficiently deliver light to and from optical cell 64.

A computer or processing module 98 may be used to take the outputs from the spectrometer 96 and other sensors such as temperature sensor 86 and pressure sensor 84 in order to determine the energy content associated with the gas flow 26.

Figure 4:
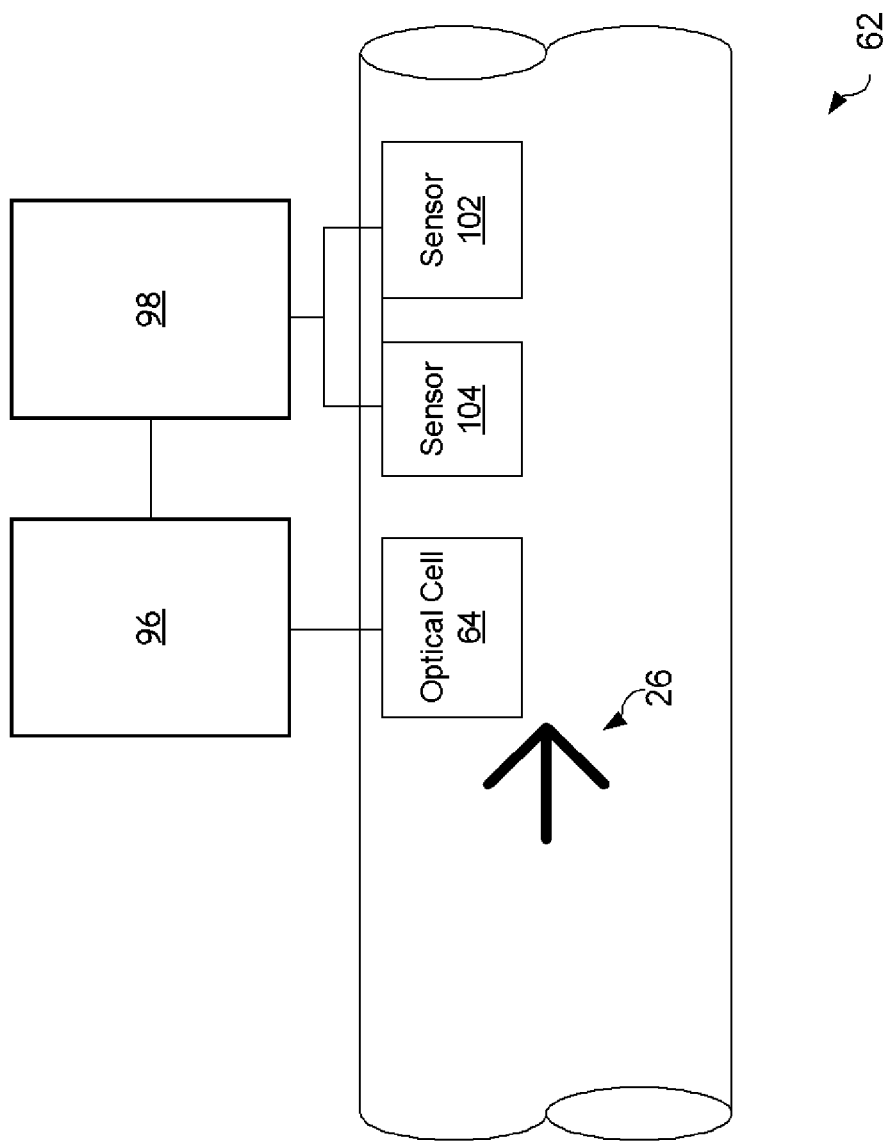
FIG. 4 depicts another embodiment of the present invention wherein the optical cell is located within the gas flow in accordance with an embodiment of the present invention in order to eliminate many of the complexities associated with an external sample system.

FIG. 4 depicts a second embodiment wherein the optical cell 64 is located within gas flow 26. This eliminates much of the need for low pressure lines and high pressure lines. In addition to optical cell 64 other sensors such as pressure sensor 102 and temperature sensor 104 may be located within gas flow 26 as well. As shown previously, the optical cell may be optically coupled using fiber optics or other like materials to spectrometer 96. Sensors 102, 104 as well as spectrometer 96 may all be communicatively coupled to a processing module 98 which may then determine the chemical composition associated with gas flow. These individual modules may be coupled wirelessly or via wired connections.

Spectrographs use chemometeric models and other analytical techniques to determine the composition of the gas. The data models are used to compare the spectrums being gathered by the spectrograph from the gas flowing through the sample cell with known results. Pressure and temperature will be recorded to account for their effects. Any offsets or adjustments required will be included in the calibration models. All of this information is compiled and used as a reference to compare the information coming from the on-line monitor. The calibration set allows one to derive the sample's energy content in both dry and saturated states, compressibility, hydrocarbon dew point, specific gravity, moisture content and Wobbe index. The models may reside on each individual installation or on a central server. The units with all the analytical capabilities on-board will send compiled data while other units may transmit raw telemetry that will be analyzed by a central server. The server will have the chemometric models and other analytical software necessary to complete the analysis.

The efficiencies enabled by a distributed network spectrographs that provide on-line data create a new battery of decision making matrices with many different permutations. Some examples include:

1. Contract Adherence:

Natural Gas suppliers and purchasing agents agree to certain quality stipulations of the gas that is being transacted. The spectrometers will be able to immediately determine if certain properties are out of contractual specifications. Examples of properties monitored are hydrocarbon dew point, moisture content and impurities. Chemical composition may change and alter the hydrocarbon dew point of the gas which may result in equipment damage and hydrocarbon drop out (condensation) down the line. The hydrocarbon condensation will result in lost energy in the transmission system and act as a catalyst for corrosion. Some examples of impurities are carbon dioxide, nitrogen, water, and hydrogen sulfide. This information may invoke a certain discounted price or penalty while the gas remains out of a premium price quality standard.

2. Process Optimization:

Gas processing plants run different process configurations based on current market conditions and the attributes of the raw material feeds. Real-time data provided by the spectrometers will enable processing plants to quickly react to changes in the composition of the gas entering the plant. This will allow these processing facilities to optimize the processes running and operate at a much greater efficiency than is currently possible. Similarly, in field processing equipment such as scrubber filters may be selectively placed on service based on the quality of the gas.

Large natural gas consumers such as electrical utilities and cement producers may adjust the burners based on changes in composition in order to optimize their processes and ensure the quality of the products they produce. As little as a 50 BTU fluctuation will have a profound impact of the performance of a burner.

3. Field Production Efficiency/Reservoir Management:

As oil and gas producing fields age, the wells need maintenance and service. The streaming data from the spectrometers will inform personnel when a well is losing productive efficiency or if another problem exists. A decision can be made on what kind of service a well is going to need or if a new zone needs to be perforated. Wells may be taken off-line or brought back on-line based on the quality of the gas coming out of the well at the time and the current market price for such gas.

4. Historical Trending and Present Value Calculations:

The information from the spectrographs can be stored on a data server where the data can be processed for historical trending. The trends can be used to characterize wells and production fields for valuation purposes and production schedules. The information may also be used to determine if drilling more wells is economically viable.

5. Payment Terms:

Data servers can store the information during payment cycles. The data can then be compiled into a report where the value of the payment can be determined. The reports may be printed and mailed or distributed electronically. The information can also be used to adhere to any sort of regulatory filings required. Clients will have the ability to access a reporting server via the internet.

Figure 5:
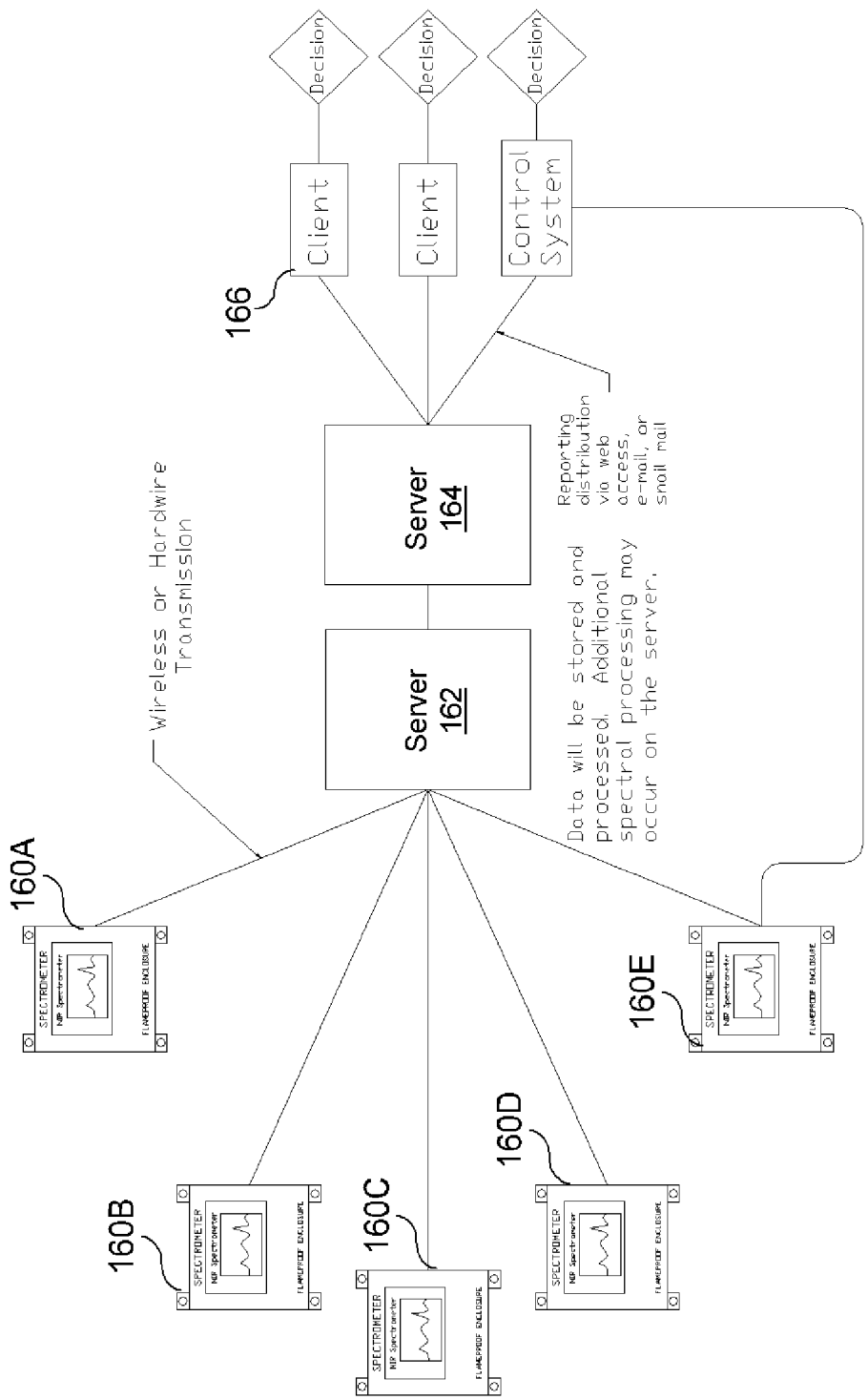
FIG. 5 shows a distributed network in accordance with an embodiment of the present invention where the sensor systems may be located at various nodes within the transmission infrastructure and collection infrastructure.

The systems as shown in the previous FIGs. may be used to determine the chemical composition or energy content of gas flow 10 in near real time at discreet locations within a gas collection and transmission infrastructure. FIG. 5 shows a distributed network where the sensor systems 160A through 160E may be located at various nodes within the transmission infrastructure or at various collection points within the collection infrastructure. For example individual wells may have these data collection systems attached to the output attached placed such that the energy content and chemical composition associated with the output of an individual well may be determined. This is important as it may identify the production capabilities and qualities of an individual well or reservoir. This information may also be used to determine when a need exists to perform maintenance or repair tasks associated with a well in order to improve the quality and content of the natural gas produced therein.

Remote sensors system 160A through 160E may be coupled to a data gathering server 162. This server will allow data to be stored and processed. Additionally should a need exist to off load spectral processing of data gathered by the spectrometer sensing systems remotely located within the gas collection transmission infrastructure, additional processing capabilities at the data gathering server 162 may be used to determine the chemical composition and energy content of the natural gas. The reporting server 164 having access to the data gathering server may then use the data or provide the data to client applications 166 from the individual collection points to determine the need for maintenance, the pricing structure based on the quality and content of the natural gas, or other like needs. For example natural gases delivered to a processing refinery may be delivered with real time chemical composition and energy content information such that the individual processing modules within the refinery may be reconfigured based on the actual raw material feed composition as opposed to standard process practices which less frequently sample the gases and can result in non-optimal configurations at manufacturing facilities when processing the natural gas. In another embodiment the information delivered to the client may be used to determine in real time the energy content end associated price associated with the natural gas delivered to an end user such as a utility.

Figure 6:
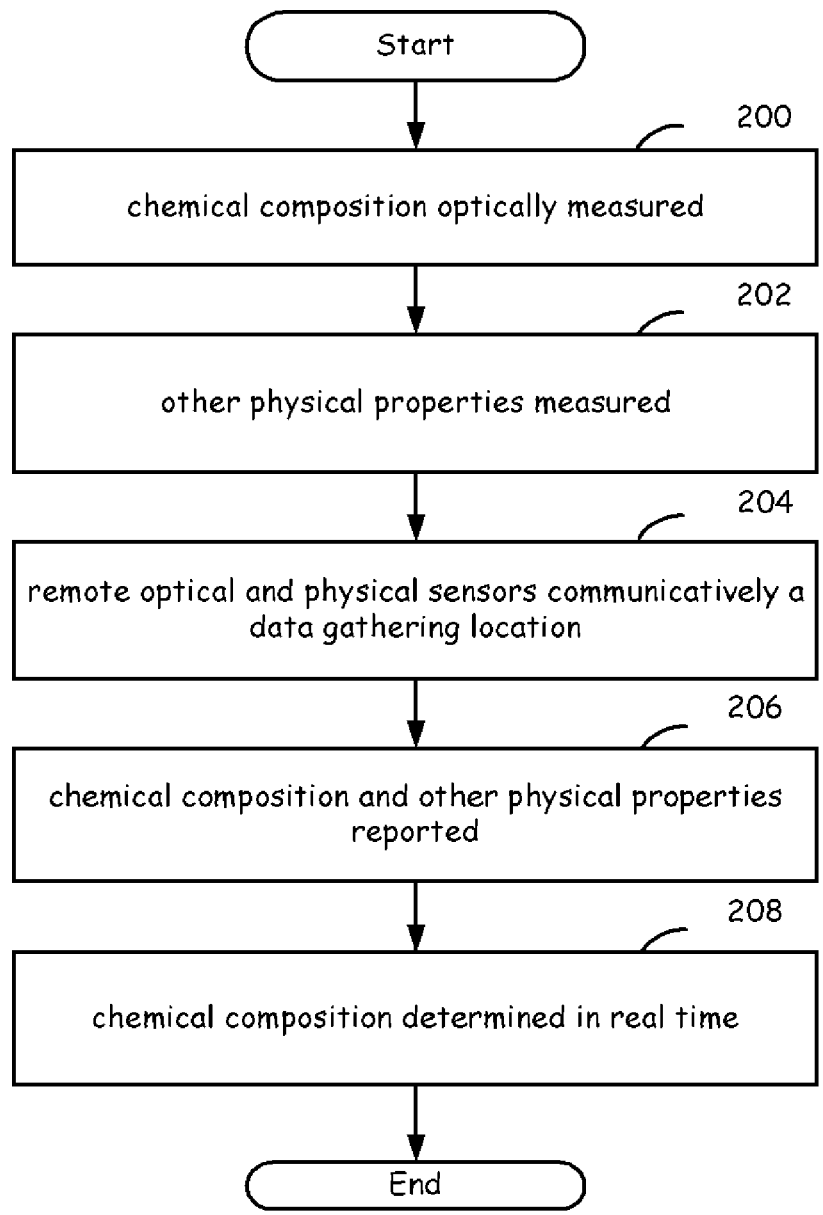
FIG. 6 provides a logic flow diagram in accordance with an embodiment of the present invention that describes how the chemical properties of a gas may be determined using remote optical sensors.

FIG. 6 provides logic flow diagram end a method to optically determine the chemical composition of the natural gas in accordance with embodiments in the present invention. In Step 200 the chemical composition of the natural gas may be optically measured using remote optical sensors within a gas collection and transmission infrastructure. In Step 202 other physical properties associated with the natural gas may be measured. These properties may include temperature and pressure but are not so limited. The chemical composition may be based on the spectrographic analysis performed using remote optical sensors. This information is combined with information such as pressure and temperature to determine overall energy content associated with the gas. The remote optical and physical sensors may be communicatively coupled in Step 204 to a data gathering location. In Step 206 the chemical composition of the natural gas as well as the other physical properties may be reported to a computer processor which may be located locally or at the data gathering location. In Step 208 the chemical composition associated with bulk quantities of the natural gas may then be determined in real time. For example using spectrographic analysis it may be possible to perform samples as often as every 20 milliseconds. This differs greatly from current practices wherein samples are taken perhaps on a monthly or quarterly basis. This analysis allows natural gas to be priced using real time chemical compositions associated with bulk quantities of the gas within the gas collection and transmission infrastructure. Another embodiment allows the downstream user to access this information in order to reconfigure manufacturing processes based on real time chemical compositions of the natural gas to be delivered. Yet another embodiment allows this methodology to be applied in the field or gathering location wherein scrubbing and filtering equipment may be placed on or off service based on the quality and contaminants contained within the gas being supplied to and delivered from the gathering location.

In summary the present invention provides a chemical composition analyzer that may be used to optically determine and report chemical compositions associated with natural gases within a gas collection and transmission infrastructure. Once the composition is known, properties of interest can be calculated for the gas. This analyzer includes a number of remote optical sensors which may be used to perform spectroscopic spectrographic analysis in order to determine the chemical composition of the natural gas. Additionally other sensors may be used to measure other physical properties associated with the natural gas. These sensors are tied to a data collection system wherein the output of the remote optical sensors and sensors used to measure the physical properties of the natural gas may be combined and processed in order to determine in a nearly continuous fashion the chemical composition associated with the natural gas at various locations within the gas collection and transmission infrastructure.

Although the present invention is described in detail, it should be understood that various changes, substitutions and alterations can be made hereto without departing from the spirit and scope of the invention as described by the appended claims.

What is claimed is:

1. A method to optically determine and report a chemical composition of a hydrocarbon comprising:
   measuring the chemical composition of the natural gas within a gas collection and transmission infrastructure with optical sensors operable to scan the natural gas with all or substantially all of the range between 1300 nm and 2500 nm of the electromagnetic spectrum with a tunable light source;
   measuring other physical properties associated with the natural gas within the gas collection and transmission infrastructure;
   communicatively coupling the optical sensors to a data gathering location;
   reporting the chemical composition of the natural gas and the other physical properties associated with the natural gas to the data gathering location; and
   determining in real time the chemical composition associated with bulk quantities of natural gas within the gas collection and transmission infrastructure.

2. The method of claim 1, wherein the optical sensors perform spectrographic analysis within said range between 1300 nm and 2500 nm of the electromagnetic spectrum.

3. The method of claim 2, wherein the spectrographic analysis is performed within the 1550 nm to 1800 nm range.

4. The method of claim 1, wherein the optical sensors comprise an optical cell coupled to the gas collection and transmission infrastructure.

5. The method of claim 1, wherein the natural gas is priced using real time chemical compositions associated with bulk quantities of natural gas.

6. The method of claim 1, wherein a downstream user reconfigures manufacturing processes based on the real time chemical compositions associated with bulk quantities of natural gas.

7. The method of claim 1, wherein a need for gas collection and transmission infrastructure maintenance is based on the real time chemical compositions associated with bulk quantities of natural gas.

8. The method of claim 1, wherein the presence of impurities within the natural gas is determined with the optical sensors.

9. The method in claim 1, wherein an overall quality of the natural gas is monitored to insure contractual compliance between a buyer and a seller.

10. The method in claim 1, wherein a natural gas producing reservoir is characterized based on the historical output of the optical sensors to determine production and drilling schedules in an effort to maximize an economic value of the gas producing reservoir.

11. The method in claim 1, wherein a natural gas producing reservoir is valued based on a historical output of the optical sensors.

12. A chemical composition analyzer operable to optically determine and report the chemical composition of a natural gas within a gas collection and transmission infrastructure, comprising:
   at least one optical sensor operable to scan the natural gas with all or substantially all of the range between 1300 nm and 2500 nm of the electromagnetic spectrum with a tunable light source to measure the chemical composition of the natural gas;
   at least one physical property sensor to measure physical properties of the natural gas; and
   a data collection system coupled to the at least one optical sensors and at least one physical property sensor, wherein the data collection system collects outputs of the at least one optical sensors and at least one physical property sensor to determine in near real time the chemical composition associated with bulk quantities of natural gas within the gas collection and transmission infrastructure.

13. The chemical composition analyzer of claim 12, wherein the optical sensors perform spectrographic analysis within said range between 1300 nm and 2500 nm of the electromagnetic spectrum.

14. The chemical composition analyzer of claim 13, wherein the spectrographic analysis is performed within the 1550 nm to 1800 nm range.

15. The chemical composition analyzer of claim 12, wherein the optical sensors comprise an optical cell coupled to the gas collection and transmission infrastructure.

16. The chemical composition analyzer of claim 12, wherein the natural gas is priced using real time chemical compositions associated with bulk quantities of natural gas.

17. The chemical composition analyzer of claim 12, wherein a downstream user reconfigures manufacturing processes based on the real time chemical compositions associated with bulk quantities of natural gas.

18. The chemical composition analyzer of claim 12, wherein a need for gas collection and transmission infrastructure maintenance is identified based on the analysis of real time chemical compositions associated with bulk quantities of natural gas.

19. The chemical composition analyzer of claim 12, wherein the presence of impurities within the natural gas is determined with the optical sensors.

20. The chemical composition analyzer of claim 12, wherein an overall quality of the natural gas is monitored to insure contractual compliance between a buyer and a seller.

21. A method to schedule maintenance within a gas collection infrastructure, the method comprising:

measuring the chemical composition of the natural gas within the gas collection and transmission infrastructure with optical sensors operable to scan the natural gas with all or substantially all of the range between 1300 nm and 2500 nm of the electromagnetic spectrum with a tunable light source and perform spectrographic analysis within said range between 1300 nm and 2500 nm of the electromagnetic spectrum;

measuring other physical properties associated with the natural gas within the gas collection and transmission infrastructure;

communicatively coupling the optical sensors to a data gathering location;

reporting the chemical composition of the natural gas and the other physical properties associated with the natural gas to the data gathering location;

determining the chemical composition associated with the natural gas within the gas collection and transmission infrastructure; and determining a need maintenance action within the gas collection infrastructure based on the chemical composition.

22. A method to price bulk quantities of natural gas within a gas collection and transmission infrastructure the method comprising:

measuring the chemical composition of the natural gas within the gas collection and transmission infrastructure with optical sensors operable to scan the natural gas with all or substantially all of the range between 1300 nm and 2500 nm of the electromagnetic spectrum with a tunable light source and perform spectrographic analysis within said range between 1300 nm and 2500 nm of the electromagnetic spectrum;

measuring other physical properties associated with the natural gas within the gas collection and transmission infrastructure;

communicatively coupling the optical sensors to a data gathering location;

reporting the chemical composition of the natural gas and the other physical properties associated with the natural gas to the data gathering location;

determining the chemical composition associated with the natural gas within the gas collection and transmission infrastructure; and pricing the natural gas within the gas collection and transmission infrastructure based on the chemical composition.

23. The method of claim 22, wherein the spectrographic analysis is performed within the 1550 nm to 1800 nm range.

24. The method of claim 2, wherein a downstream user reconfigures manufacturing processes based on the real time chemical compositions associated with the natural gas.

25. A method comprising:

optically determining a chemical composition of a hydrocarbon mixture with optical sensors operable to scan the natural gas with all or substantially all of the range between 1300 nm and 2500 nm of the electromagnetic spectrum with a tunable light source using real time spectrographic analysis performed in near infrared (NIR), the hydrocarbon mixture within a gas collection, transmission and processing infrastructure;

measuring other physical properties associated with the hydrocarbon mixture within the gas collection and transmission infrastructure;

communicatively coupling the optical sensors to a data gathering location;

reporting the chemical composition of the hydrocarbon mixture and the other physical properties associated with the hydrocarbon mixture to the data gathering location; and determining in real time the chemical composition associated with bulk quantities of hydrocarbon mixture within the gas collection, transmission and processing infrastructure.

26. The method of claim 25, further comprising: adjusting a processing configuration of gas processing modules within the gas collection, transmission and processing infrastructure based on the chemical composition of the hydrocarbon mixture as determined in real time.

27. The method of claim 1, wherein the optical sensors perform spectrographic analysis over a continuous scan of said range between 1300 nm and 2500 nm of the electromagnetic spectrum.

* * * * *